US008244556B1

(12) United States Patent
Ringold

(10) Patent No.: US 8,244,556 B1
(45) Date of Patent: Aug. 14, 2012

(54) SYSTEMS AND METHODS FOR GENERATING PAYOR SHEETS ASSOCIATED WITH PAYORS FOR HEALTHCARE TRANSACTIONS

(75) Inventor: James Morgan Ringold, Lawrenceville, GA (US)

(73) Assignee: McKesson Financial Holdings Limited, Hamilton (BM)

( * ) Notice: Subject to any disclaimer, the term of this patent is extended or adjusted under 35 U.S.C. 154(b) by 233 days.

(21) Appl. No.: 12/821,830

(22) Filed: Jun. 23, 2010

(51) Int. Cl.
*G06Q 10/00* (2012.01)
*G06Q 50/00* (2012.01)
(52) U.S. Cl. .............................................. 705/2; 705/3
(58) Field of Classification Search .................... 705/2, 3
See application file for complete search history.

(56) References Cited

U.S. PATENT DOCUMENTS

| | | | |
|---|---|---|---|
| 5,628,530 | A | 5/1997 | Thornton |
| 6,012,035 | A | 1/2000 | Freeman et al. |
| 6,195,612 | B1 | 2/2001 | Pack-Harris |
| 6,757,898 | B1 | 6/2004 | Ilsen et al. |
| 6,769,228 | B1 | 8/2004 | Mahar |
| 7,155,397 | B2 | 12/2006 | Alexander et al. |
| 7,401,027 | B2 | 7/2008 | Moore et al. |
| 2001/0037216 | A1 | 11/2001 | Oscar et al. |
| 2002/0002495 | A1 | 1/2002 | Ullman |
| 2002/0087583 | A1 | 7/2002 | Morgan et al. |
| 2002/0111832 | A1 | 8/2002 | Judge |
| 2002/0198831 | A1 | 12/2002 | Patricelli et al. |
| 2003/0009367 | A1 | 1/2003 | Morrison |
| 2003/0050799 | A1 | 3/2003 | Jay et al. |
| 2003/0149625 | A1 | 8/2003 | Leonardi et al. |
| 2003/0154163 | A1 | 8/2003 | Phillips et al. |
| 2003/0229540 | A1 | 12/2003 | Algiene |
| 2004/0006490 | A1 | 1/2004 | Gingrich et al. |
| 2004/0039599 | A1 | 2/2004 | Fralic |
| 2004/0073457 | A1 | 4/2004 | Kalies |
| 2004/0078234 | A1 | 4/2004 | Tallal, Jr. et al. |
| 2004/0117323 | A1 | 6/2004 | Mindala |
| 2004/0148198 | A1 | 7/2004 | Kalies |
| 2004/0249745 | A1 | 12/2004 | Baaren |

(Continued)

FOREIGN PATENT DOCUMENTS

CA    2482370 A1    3/2006

(Continued)

OTHER PUBLICATIONS

Sampson, R.J., Taking Control of Health Care Costs, Best's Review—Life Health Insurance Edition, Nov. 1983, pp. 64-66, vol. 84, Issue 7, USA.

(Continued)

*Primary Examiner* — Neal Sereboff
(74) *Attorney, Agent, or Firm* — Sutherland Asbill & Brennan LLP

(57) ABSTRACT

Systems and methods are provided for generating payor sheets associated with payors for healthcare transactions. Information associated with one or more healthcare transactions that have been processed by a payor may be obtained. A plurality of data fields included in the one or more healthcare transactions may be identified, and a respective usage of each of the identified data fields within the one or more healthcare transactions may be calculated. Based upon the calculated usages, one or more of the plurality of data fields may be identified as required fields. A required field may be a field required by the payor during the submission of a healthcare transaction. Based at least in part upon the identified one or more required fields, a payor sheet associated with the payor may be generated.

20 Claims, 5 Drawing Sheets

U.S. PATENT DOCUMENTS

| | | |
|---|---|---|
| 2005/0015280 A1 | 1/2005 | Gabel et al. |
| 2005/0060201 A1 | 3/2005 | Connely, III et al. |
| 2005/0102169 A1 | 5/2005 | Wilson |
| 2005/0154627 A1 | 7/2005 | Zuzek et al. |
| 2005/0187793 A1 | 8/2005 | Myles |
| 2005/0197862 A1 | 9/2005 | Paterson et al. |
| 2005/0240473 A1 | 10/2005 | Ayers, Jr. et al. |
| 2005/0288972 A1 | 12/2005 | Marvin et al. |
| 2006/0020514 A1 | 1/2006 | Yered |
| 2006/0026041 A1 | 2/2006 | Ullman |
| 2006/0085230 A1 | 4/2006 | Brill et al. |
| 2006/0149784 A1 | 7/2006 | Tholl et al. |
| 2006/0184391 A1 | 8/2006 | Barre et al. |
| 2006/0259363 A1 | 11/2006 | Jhetam et al. |
| 2007/0005402 A1 | 1/2007 | Kennedy et al. |
| 2007/0050209 A1 | 3/2007 | Yered |
| 2007/0136100 A1 | 6/2007 | Daugherty et al. |
| 2007/0233525 A1 | 10/2007 | Boyle |
| 2007/0233526 A1 | 10/2007 | Hoffman et al. |
| 2007/0239493 A1 | 10/2007 | Sweetland et al. |

FOREIGN PATENT DOCUMENTS

| | | | |
|---|---|---|---|
| WO | WO9503569 | A3 | 2/1995 |
| WO | WO0039737 | A1 | 7/2000 |
| WO | WO2007025295 | A2 | 3/2007 |

OTHER PUBLICATIONS

Anonymous, ACS to Demonstrate Electronic Health Record Solution Suite at MMIS 2007 Conference; EHR Tools Consolidate Data, Provide Useful information at the Point of Care for Medicaid Providers, Payers, and Patients, PR Newswire, Aug. 13, 2007, New York, NY, USA.

Lamb, J., New Era of Electronic Medicine Management: E-Prescriptions, Britain's Traditionally Cautious National Health Service is Starting Trials for Online Prescription, with the Aim of Cutting Costs, Financial Times, London, Feb. 21, 2001, p. 6, London, United Kingdom.

Anonymous, Pharmacy Industry Leaders Launch Firm to Supply Real-Time Data. PR Newswire. Jul. 30, 2001, p. 1, New York, NY, USA.

Anonymous, Medic; On-line Goes In-House, Chain Store Age Executive, Jan. 1987, pp. 128-132. vol, 63, Issue 1, USA.

Anonymous, TechRx Announces Successful Beta Deployment of T-Rex. PR Newswire. May 13, 2002.

Final Office Action for U.S. Appl. No. 11/759,767 mailed Dec. 24, 2009.

Non-Final Office Action for U.S. Appl. No. 11/759,767 mailed Jul. 9, 2009.

SYSTEMS AND METHODS FOR GENERATING PAYOR SHEETS ASSOCIATED WITH PAYORS FOR HEALTHCARE TRANSACTIONS

FIELD OF THE INVENTION

Aspects of the invention relate generally to healthcare transactions, and more particularly, to the generation of payor sheets associated with payors for healthcare transactions.

BACKGROUND OF THE INVENTION

Healthcare providers, such as pharmacies, physicians, and/or hospitals, often generate healthcare transactions, such as healthcare claim transactions, that are communicated, to appropriate claims processors or payors, such as insurance providers or government payors, for approval. In order to ensure compliance with the Health Insurance Portability and Accountability Act ("HIPAA"), healthcare providers often desire to include only necessary or required data when preparing a healthcare transaction to be communicated to a payor. Each payor typically has a proprietary mixture of data fields required to be populated by a healthcare provider when a healthcare transaction is communicated to the payor.

Payors typically publish information associated with required data fields in respective payor sheets. However, payors often fail to update or maintain their payor sheets in a timely manner. Accordingly, as new data fields are required and/or other data fields are no longer required, the published payor sheets may become outdated and a healthcare provider may not be able to readily ascertain the information that is required to be included in a healthcare transaction. Additionally, when a healthcare provider purchases and/or installs a new practice management system, the healthcare provider is often required to start from scratch in building one or more plan setups. In other words, the healthcare provider typically has to engage in a time consuming process to generate forms that can be populated by employees when preparing healthcare transactions.

Therefore, systems and methods for generating and/or updating payor sheets are desirable.

BRIEF DESCRIPTION OF THE INVENTION

Some or all of the above needs and/or problems may be addressed by certain embodiments of the invention. Embodiments of the invention may include systems, methods, and apparatus for generating payor sheets associated with payors for healthcare transactions. In one embodiment, a method for generating a payor sheet is provided. Information associated with one or more healthcare transactions that have been processed by a payor may be obtained. A plurality of data fields included in the one or more healthcare transactions may be identified, and a respective usage of each of the identified data fields within the one or more healthcare transactions may be calculated. Based upon the calculated usages, one or more of the plurality of data fields may be identified as required fields. A required field may be a field required by the payor during the submission of a healthcare transaction. Based at least in part upon the identified one or more required fields, a payor sheet associated with the payor may be generated. In certain embodiments, the above operations may be performed by one or more computers associated with a service provider.

In accordance with another embodiment of the invention, a system for the generation of a payor sheet is provided. The system may include at least one memory and at least one processor. The at least one memory may be operable to store computer-executable instructions. The at least one processor may be configured or programmed to access the at least one memory and execute the computer-executable instructions to: obtain information associated with one or more healthcare transactions that have been processed by a payor; identify a plurality of data fields included in the one or more healthcare transactions; calculate a respective usage of each of the identified data fields within the one or more healthcare transactions; identify, based upon the calculated usages, one or more of the plurality of data fields as required fields, wherein a required field is a field required by the payor during the submission of a healthcare transaction; and generate, based at least in part upon the identified one or more required fields, a payor sheet associated with the payor.

In accordance with yet another embodiment of the invention, a method for generating a payor sheet is provided. Information associated with a plurality of healthcare transactions that are communicated between one or more healthcare providers and one or more payors may be stored by a service provider. Based upon one or more parameters associated with the generation of a payor sheet, a subset of the plurality of healthcare transactions that are associated with a payor may be accessed. A plurality of data fields included in the accessed subset of healthcare transactions may be identified. A respective usage of each of the identified data fields within the subset of healthcare transactions may be calculated. Based upon the calculated usages, one or more of the plurality of data fields may be identified as required fields. A required field may be a field required by the payor during the submission of a healthcare transaction. Based at least in part upon the identified one or more required fields, a payor sheet associated with the payor may be generated. In certain embodiments, the above operations may be performed by one or more computers associated with a service provider.

Additional systems, methods, apparatus, features, and aspects may be realized through the techniques of various embodiments of the invention. Other embodiments and aspects of the invention are described in detail herein with reference to the description and to the drawings and are considered a part of the claimed invention.

BRIEF DESCRIPTION OF THE DRAWINGS

Reference will now be made to the accompanying drawings, which are not necessarily drawn to scale, and wherein.

DETAILED DESCRIPTION

Figure 1:
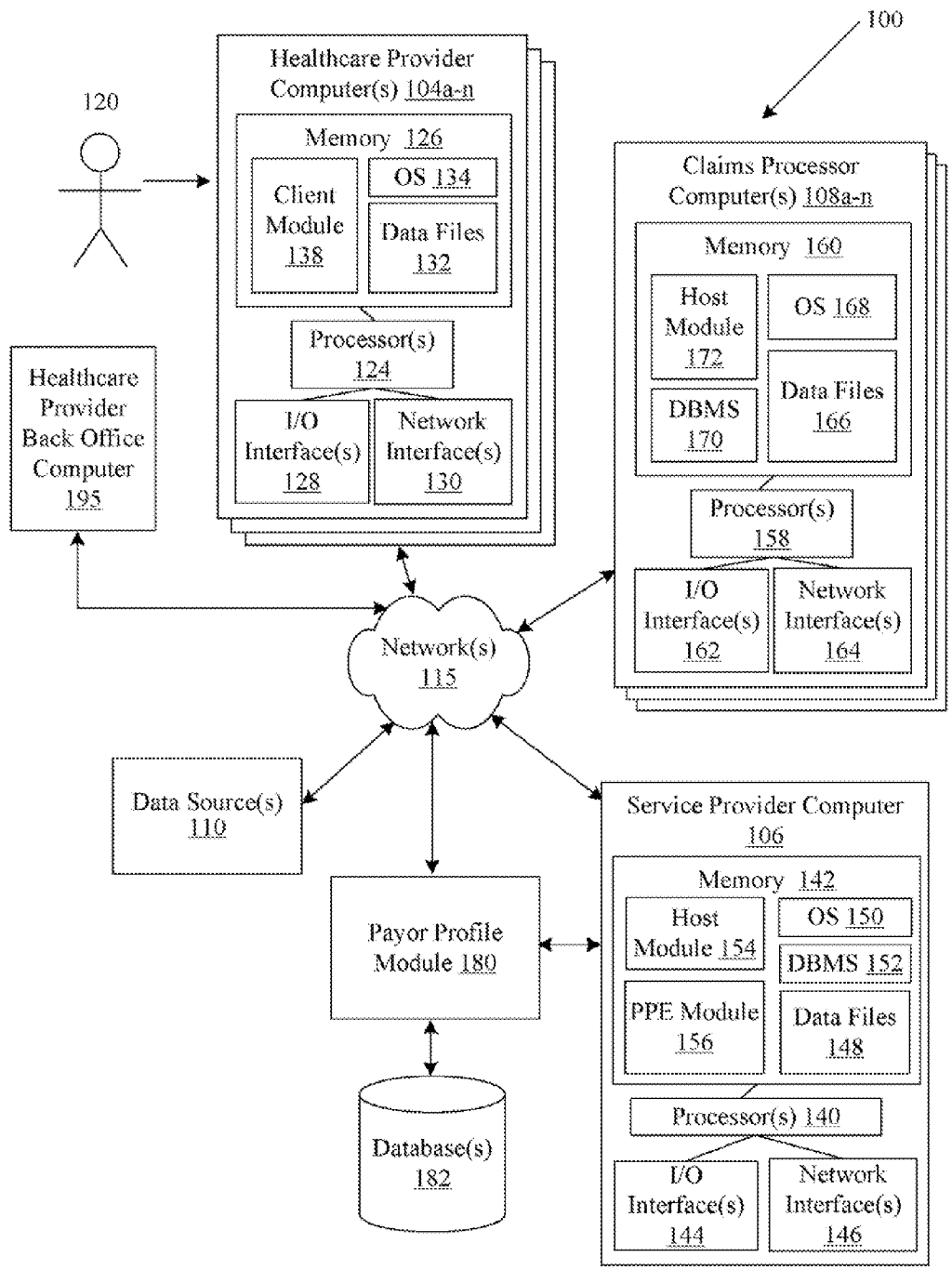
FIG. 1 illustrates an example overview of a system that facilitates the generation of payor sheets, according to an example embodiment of the invention.

Embodiments of the invention now will be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Embodiments of the invention may include systems, methods, and apparatus for the generation of payor sheets for one or more payors of healthcare transactions, such as one or more insurance providers or government payors. In certain embodiments, information associated with one or more healthcare transactions that have been processed by a payor or claims processor may be obtained by a service provider. The information may include information stored by the service provider and/or information obtained from one or more external data sources. For example, the service provider may access stored records associated with healthcare transactions that have been routed to the payor by the service provider. As another example, the service provider may receive, from an external data source, information associated with healthcare transactions that have been processed or adjudicated by the payor. Additionally, as desired, the information may be obtained based upon any number of rules or parameters associated with the generation of the payor sheet, such as parameters identifying the payor, parameters identifying a relevant time period for obtaining information, etc. Once the information has been obtained, a plurality of data fields included in the one or more healthcare transactions may be identified. For example, the data fields that have been populated in one or more of the transactions may be identified. A respective usage of each of the identified data fields may then be calculated. For example, a percentage usage or a percentage population of each identified data field may be calculated. Based upon the calculated usages, one or more of the plurality of data fields may be identified as required fields. For example, a calculated usage may be compared to a threshold parameter in order to determine whether a data field is a required field. A required field may be a field required by the payor during the submission of a healthcare transaction. In addition to identifying required fields based upon calculated usages, required fields may be identified based upon an analysis of one or more healthcare transactions that have been rejected by the payor. For example, a transaction that has been rejected by the payor for failing to include information in a data field or for including incorrect information in the data field may be identified. The relevant data field that led to the rejection may then be identified as a required field. Based at least in part upon the identified one or more required fields, a payor sheet associated with the payor may be generated.

In certain embodiments, payor sheets may be generated and/or maintained dynamically by the service provider. In other embodiments, payor sheets may be periodically generated by the service provider. For example, a payor sheet may be generated and/or updated once a day, once a week, etc. In yet other embodiments, payor sheets may be generated upon request. For example, a payor sheet may be generated based upon a request that is received from a healthcare provider. Following the generation of a payor sheet, the payor sheet may be communicated to any number of recipients. For example, the generated payor sheet may be communicated to a healthcare provider. As another example, the generated payor sheet may be communicated to a healthcare provider that is installing and/or implementing a new practice management system. As desired, the payor sheet may be communicated by itself or in combination with other information, such as payor sheets for other payors. Additionally, the generated payor sheet may be utilized to prepare one or more forms or presentations that facilitate the preparation of a healthcare transaction to communicate to the payor. For example, the payor sheet may be utilized to generate a fillable form or presentation, such as a form that is utilized by a pharmacy practice management system, that may be utilized by an employee of a healthcare provider to prepare a healthcare transaction.

System Overview

An example system 100 for facilitating the generation of payor sheets will now be described illustratively with respect to FIG. 1. As shown in FIG. 1, the system 100 may include one or more healthcare provider computers 104*a*-*n*, service provider computers 106, and claims processor computers 108*a*-*n*. As desired, each of the healthcare provider computers 104*a*-*n*, service provider computer 106, and claims processor computers 108*a*-*n* may include one or more processing devices that may be configured for accessing and reading associated computer-readable media having stored thereon data and/or computer-executable instructions for implementing the various methods of the invention.

Additionally, in certain embodiments, the service provider computer 106 may include or otherwise be in communication with a payor profile module 180 or a payor profile application, which may access and/or be in communication with one or more suitable data storage devices 182 and/or databases. The payor profile module 180 may access or otherwise obtain information associated with one or more healthcare transactions that have been processed by one or more payors or claims processors. The payor profile module 180 may analyze the healthcare transaction information in order to generate one or more respective payor sheets for the payors. For example, the payor profile module 180 may access information associated with healthcare claim transactions that have been routed through the service provider computer 106 to a payor for adjudication. As another example, the payor profile module 180 may obtain, from one or more external data sources 110, information associated with healthcare claim transactions that have been adjudicated by the payor.

Accessed and/or obtained information may be analyzed by the payor profile module 180 in order to identify fields that are required by the payor to be populated when a healthcare transaction is submitted to the payor. A wide variety of suitable techniques may be utilized to analyze one or more required fields associated with the payor. For example, fields that are populated in the analyzed healthcare transactions may be identified, and a usage for each identified field may be calculated. The respective calculated usage for each field may then be compared to a predetermined threshold value in order to determine whether the field is likely a required field. As another example, healthcare transactions that have been rejected by the payor based at least in part upon a failure to include information in one or more fields or an inclusion of incorrect information in one or more fields may be identified. The relevant fields that led to the rejection(s) by the payor may then be identified as required fields. Once the required field(s) for a payor have been identified, the payor profile module 180 may utilize the identified required fields to generate and/or update a payor sheet for the payor. A generated payor sheet may, then be communicated by the payor profile module 180 or at the direction of the payor profile module 180 to one or more recipients, such as one or more healthcare provider computers 104*a*-*n*. In this regard, current or up-to-date payor sheets may be provided to one or more healthcare providers, thereby improving the work flow of the healthcare providers and reducing rejections of healthcare transactions that are prepared by the healthcare providers for submission to payors.

Generally, network devices and systems, including one or more of the healthcare provider computers 104a-n, service provider computer 106, and claims processor computers 108a-n may include or otherwise be associated with suitable hardware and/or software for transmitting and receiving data and/or computer-executable instructions over one or more communications links or networks. These network devices and systems may also include any number of processors for processing data and executing computer-executable instructions, as well as other internal and peripheral components that are well-known in the art. Further, these network devices and systems may include or be in communication with any number of suitable memory devices operable to store data and/or computer-executable instructions. By executing computer-executable instructions, each of the network devices may form a special purpose computer or particular machine. As used herein, the term "computer-readable medium" describes any form of suitable memory or memory device.

As shown in FIG. 1, the healthcare provider computers 104a-n, service provider computer 106, and claims processor computers 108a-n may be in communication with each other via one or more networks, such as network 115, which as described below can include one or more separate or shared private and public networks, including the Internet or a publicly switched telephone network. Each of these components—the healthcare provider computers 104a-n, service provider computer 106, claims processor computers 108a-n, and the network 115—will now be discussed in further detail.

Any number of healthcare provider computers 104a-n may be provided. Each healthcare provider computer (generally referred to as a healthcare provider computer 104) may be associated with a healthcare provider, for example, a pharmacy, physician's office, hospital, etc. The healthcare provider computer 104 may be any suitable processor-driven device that facilitates the processing of healthcare requests (e.g., prescription orders) made by or on behalf of patients or consumers and the communication of information associated with healthcare transaction requests (e.g., healthcare claim transactions, healthcare claim requests, eligibility transaction requests, etc.) to the service provider computer 106. The healthcare provider computer 104 may additionally facilitate the receipt of responses to healthcare transactions and/or the receipt of payor sheets and/or information associated with payor sheets. For example, the healthcare provider computer 104 may be a computing device that includes any number of server computers, mainframe computers, networked computers, desktop computers, personal computers, digital assistants, personal digital assistants, digital tablets, Internet appliances, application-specific circuits, microcontrollers, minicomputers, and/or any other processor-based device(s). In certain embodiments, the healthcare provider computer 104 may be a suitable point of sale device associated with a healthcare provider. The execution of the computer-implemented instructions by the healthcare provider computer 104 may form a special purpose computer or other particular machine that is operable to facilitate the processing of healthcare requests (e.g., prescription orders) made by or on behalf of patients and the communication of information associated with healthcare transaction requests (e.g., claim requests and/or healthcare claim transactions, eligibility transaction requests, etc.) to a service provider computer 106. Additionally, in certain embodiments of the invention, the operations and/or control of the healthcare provider computer 104 may be distributed among several processing components.

In addition to having one or more processors 124, the healthcare provider computer 104 may include one or more memory devices 126, one or more input/output ("I/O") interfaces 128, and one or more network interfaces 130. The memory devices 126 may be any suitable memory device, for example, caches, read-only memory devices, random access memory devices, magnetic storage devices, removable storage devices, etc. The memory devices 126 may store data, executable instructions, and/or various program modules utilized by the healthcare provider computer 104, for example, data files 132, an operating system ("OS") 134, and/or a client module 138. The data files 132 may include any suitable data that facilitates the receipt and/or processing of healthcare requests (e.g., prescription orders) by the healthcare provider computer 104 and the generation and/or processing of healthcare transaction requests (e.g., healthcare claim requests, healthcare claim transactions, eligibility transaction requests, etc.) that are communicated to the service provider computer 106. For example, the data files 132 may include, but are not limited to, information associated with the service provider computer 106, information associated with one or more claims processors or payors, and/or information associated with one or more healthcare transaction requests. The OS 134 may be a suitable software module that controls the general operation of the healthcare provider computer 104. The OS 134 may also facilitate the execution of other software modules by the one or more processors 124, for example, the client module 138. The OS 134 may be, but is not limited to, Microsoft Windows®, Apple OSX™, Linux, Unix, or a mainframe operating system. The client module 138 may be an Internet browser or other software, including a dedicated program, for interacting with the service provider computer 106. In certain embodiments, the client module 138 may be a component of a transaction management system that facilitates the preparation of a healthcare transaction. For example, a user such as a pharmacist or other pharmacy employee, may utilize the client module 138 in preparing and providing a prescription claim request to the service provider computer 106 for delivery to one or more appropriate claims processor computers 108, for adjudication or other coverage/benefits determination. The healthcare provider computer 104 may also utilize the client module 138 to retrieve or otherwise receive data, messages, or responses from the service provider computer 106 and/or other components of the system 100. For example, in certain embodiments, the client module 138 may be utilized to receive generated payor sheets and/or information associated with payor sheets.

In operation, the healthcare provider computer 104 may receive information associated with a healthcare request (e.g., prescription order) from a patient. As one example, the healthcare provider computer 104 may receive information associated with a healthcare request for a patient at a point of sale, such as in a pharmacy during a prescription fulfillment or purchase transaction or at a physician's office during the provision of a healthcare service. As another example, the healthcare provider computer 104 may electronically receive a healthcare request from a physician computer, a patient computer, or other patient device. The healthcare provider computer 104 may generate a healthcare transaction request (e.g., healthcare claim request, healthcare claim transaction, eligibility transaction request, etc.), and information associated with the healthcare transaction request may be communicated to the service provider computer 106. The healthcare provider computer 104 may then receive one or more responses to the healthcare transaction requests, such as an adjudicated reply for a claim transaction, a rejection message associated with a transaction, and/or one or more messages generated by the service provider computer 106. Additionally, as desired, the healthcare provider computer 104 may receive one or more payor sheets and/or information associated with payor sheets from the service provider computer 106 and/or the payor profile module 180.

The one or more I/O interfaces 128 may facilitate communication between the healthcare provider computer 104 and one or more input/output devices, for example, one or more user interface devices, such as a display, keypad, control panel, touch screen display, remote control, microphone, etc., that facilitate user interaction with the healthcare provider computer 104. For example, the one or more I/O interfaces 128 may facilitate entry of information associated with a healthcare transaction request (e.g., healthcare claim transaction, healthcare claim request, eligibility transaction request, etc.) by an employee of a healthcare provider, such as a pharmacy employee. The one or more network interfaces 130 may facilitate connection of the healthcare provider computer 104 to one or more suitable networks, for example, the network 115 illustrated in FIG. 1. In this regard, the healthcare provider computer 104 may receive and/or communicate information to other network components of the system 100, such as the service provider computer 106.

In certain embodiments, the healthcare provider computer 104 can further include a facsimile/printing device operative to receive and print one or more messages received from the service provider computer 106 and/or the payor profile module 180. For example, as described further below, the service provider computer 106 may on occasion transmit a facsimile or other printing command to the healthcare provider computer 104 and/or the facsimile/printing device containing one or more messages associated with payor sheets and/or payor profile information. The transmission from the service provider computer 106 may be directly to the facsimile/printing device, such as may be accomplished via a network 115 (e.g., Internet, cellular network, wireless network, or any other similar network, etc.). In another embodiment, the transmission may be to the healthcare provider computer 104, which in turn communicates with and commands the facsimile/printing device to print a message. Although the term facsimile/printing device is used throughout this description, it is appreciated that any other device operable to receive and print or generate a display of a notification message may be included within the scope of a facsimile/printing device. Examples of other devices include, but are not limited to, a mobile device (e.g., cellular telephone, personal digital assistant, personal information device, etc.), a personal computer, a computer kiosk, or any other handheld or mobile devices.

With continued reference to FIG. 1, the service provider computer 106 may include, but is not limited to, any suitable processor-driven device that is configured for receiving, processing, and fulfilling requests from the healthcare provider computers 104*a-n* and/or claims processor computers 108*a-n* relating to prescription, pharmacy, benefits, eligibility, and/or healthcare transactions and/or other activities. In certain embodiments, the service provider computer 106 may be a switch/router that routes healthcare transactions comprising requests and replies/responses. For example, the service provider computer 106 may route billing requests and/or prescription claim requests communicated from healthcare provider computers 104*a-n* to claims processor computers 108*a-n*, which may be associated with pharmacy benefits managers ("PBMs"), insurers, government payors, claims clearinghouses, and/or other payors. The service provider computer 106 may then route adjudicated replies or other responses to the claim requests from the claims processor computers 108*a-n* to the healthcare provider computers 104*a-n*. As desired, information associated with routed healthcare transactions and the adjudication of the transactions may be stored by the service provider computer 106 and/or the payor profile module 180. Additionally, as described in greater detail below, the service provider computer 106 and/or an associated payor profile module 180 may be configured for receiving, from one or more external data sources 110, information associated with healthcare transactions and/or the adjudication of the healthcare transactions. At least a portion of the stored and/or received healthcare transaction information may be analyzed by the payor profile module 180 and utilized to generate and/or update one or more payor sheets. In certain embodiments, the service provider computer 106 may include a suitable host server, host module, or other software that facilitates the receipt of a healthcare transaction request or reply and/or the routing of the transaction request or reply to a recipient. Any number of healthcare provider computers and/or claims processor computers may be in communication with the service provider computer 106 as desired in various embodiments of the invention.

The service provider computer 106 may include any number of special purpose computers or other particular machines, application-specific circuits, microcontrollers, personal computers, minicomputers, mainframe computers, servers, networked computers, and/or other processor-driven devices. In certain embodiments, the operations of the service provider computer 106 may be controlled by computer-executed or computer-implemented instructions that are executed by one or more processors associated with the service provider computer 106 to form a special purpose computer or other particular machine that is operable to facilitate the receipt, routing, and/or processing of healthcare transactions, such as healthcare claim requests or healthcare claim transactions. Additionally, the execution of computer-executed or computer-implemented instructions may form a special purpose computer or other particular machine that is operable to facilitate the receipt and/or access of healthcare transaction information and/or the processing of the healthcare transaction information in order to generate payor sheets. The one or more processors that control the operations of the service provider computer 106 may be incorporated into the service provider computer 106 and/or may be in communication with the service provider computer 106 via one or more suitable networks. In certain embodiments of the invention, the operations and/or control of the service provider computer 106 may be distributed among several processing components.

Similar to the healthcare provider computer 104, the service provider computer 106 may include one or more processors 140, one or more memory devices 142, one or more input/output ("I/O") interfaces 144, and one or more network interfaces 146. The one or more memory devices 142 may be any suitable memory devices, for example, caches, read-only memory devices, random access memory devices, magnetic storage devices, removable memory devices, etc. The one or more memory devices 142 may store data, executable instructions, and/or various program modules utilized by the service provider computer 106, for example, data files 148, an operating system ("OS") 150, the host module 154, a pre- and post-edit ("PPE") module 156, and a database management system ("DBMS") 152 to facilitate management of the data files 148 and other data stored in the memory devices 142 and/or one or more databases or data storage devices 182. The OS 150 may be, but is not limited to, Microsoft Windows®, Apple Linux, Unix, or a mainframe operating system. The OS 150 may be a suitable software module that controls the general operation of the service provider computer 106 and/or that facilitates the execution of other software modules.

The PPE module 156 may be operable to perform one or more pre-edits on a received healthcare transaction, such as a claim transaction, prior to routing or otherwise communicating the received healthcare transaction to a recipient, such as a claims processor computer 108. Additionally, the PPE module 156 may be operable to perform one or more post-edits on an adjudicated reply or response that is received from a claims processor computer 108 for a healthcare claim transaction prior to routing the adjudicated reply to the healthcare provider computer 104. A wide variety of different pre-edits and/or post-edits may be performed as desired in various embodiments of the invention. In certain embodiments, a pre- or post-edit may be configured to store information associated with a healthcare transaction that is routed through or processed by the service provider computer 106. A wide variety of information may be stored by a pre- or post-edit as desired in various embodiments of the invention, including but not limited to, a copy of a healthcare transaction, a copy of an adjudicated reply or other response to a healthcare transaction, information included in the healthcare transaction and/or response, etc.

According to an embodiment of the invention, the data files 148 may store healthcare transaction records associated with communications received from various healthcare provider computers 104*a-n* and/or various claims processor computers 108*a-n*. The data files 148 may also store any number of suitable routing tables that facilitate determining the destination of communications received from a healthcare provider computer 104 or claims processor computer 108. The host module 154 may receive, process, and respond to requests from the respective client modules 138 of the healthcare provider computers 104*a-n*, and may further receive, process, and respond to requests of the respective host modules 172 of the various claims processor computers 108*a-n*. The service provider computer 106 may include additional program modules for performing other processing methods described herein. Those of ordinary skill in the art will appreciate that the service provider computer 106 may include alternate and/or additional components, hardware or software without departing from example embodiments of the invention.

With continued reference to the service provider computer 106, the one or more I/O interfaces 144 may facilitate communication between the service provider computer 106 and one or more input/output devices, for example, one or more user interface devices, such as a display, keypad, control panel, touch screen display, remote control, microphone, etc., that facilitate user interaction with the service provider computer 106. The one or more network interfaces 146 may facilitate connection of the service provider computer 106 to one or more suitable networks, for example, the network 115 illustrated in FIG. 1. In this regard, the service provider computer 106 may communicate with other components of the system 100.

With continued reference to FIG. 1, any number of claims processor computers 108*a-n* may be provided. Each claims processor computer (generally referred to as claims processor computer 108) may be any suitable processor-driven device that facilitates receiving, processing, and/or fulfilling healthcare transactions, such as healthcare claim transactions, received from the service provider computer 106. For example, a claims processor computer 108 may be a processor-driven device associated with a pharmacy benefits manager ("PBM"), an insurer, a government payor, or a claims clearinghouse. As desired, the claims processor computer 108 may include any number of special purpose computers or other particular machines, application-specific circuits, microcontrollers, personal computers, minicomputers, mainframe computers, servers, and the like. In certain embodiments, the operations of a claims processor computer 108 may be controlled by computer-executed or computer-implemented instructions that are executed by one or more processors associated with the claims processor computer 108 to form a special purpose computer or other particular machine that is operable to facilitate the receipt, processing, and/or fulfillment of healthcare transaction requests received from the service provider computer 106. The one or more processors that control the operations of the claims processor computer 108 may be incorporated into the claims processor computer 108 and/or in communication with the claims processor computer 108 via one or more suitable networks. In certain embodiments of the invention, the operations and/or control of the claims processor computer 108 may be distributed among several processing components.

Similar to other components of the system 100, each claims processor computer 108 may include one or more processors 158, one or more memory devices 160, one or more input/output ("I/O") interfaces 162, and one or more network interfaces 164. The one or more memory devices 160 may be any suitable memory devices, for example, caches, read-only memory devices, random access memory devices, magnetic storage devices, removable memory devices, etc. The one or more memory devices 160 may store data, executable instructions, and/or various program modules utilized by the claims processor computer 108, for example, data files 166, an operating system ("OS") 168, a database management system ("DBMS") 170, and a host module 172. The data files 166 may include any suitable information that is utilized by the claims processor computer 108 to process healthcare transactions, for example, patient profiles, patient insurance information, other information associated with a patient, information associated with a healthcare provider, information associated with financial coverage information, etc. The OS 168 may be a suitable software module that controls the general operation of the claims processor computer 108. The OS 168 may also facilitate the execution of other software modules by the one or more processors 158, for example, the DBMS 170 and/or the host module 172. The OS 168 may be, but is not limited to, Microsoft Windows®, Apple OSX™, Linux, Unix, or a mainframe operating system. The DBMS 170 may be a suitable software module that facilitates access and management of one or more databases that are utilized to store information that is utilized by the claims processor computer 108 in various embodiments of the invention. The host module 172 may initiate, receive, process, and/or respond to healthcare transaction requests, such as healthcare claim transactions or claim requests, from the host module 154 of the service provider computer 106. Those of ordinary skill in the art will appreciate that the claims processor computer 108 may include alternate and/or additional components, hardware or software without departing from example embodiments of the invention.

The one or more I/O interfaces 162 may facilitate communication between the claims processor computer 108 and one or more input/output devices, for example, one or more user interface devices, such as a display, keypad, control panel, touch screen display, remote control, microphone, etc., that facilitate user interaction with the claims processor computer 108. The one or more network interfaces 164 may facilitate connection of the claims processor computer 108 to one or more suitable networks, for example, the network 115 illustrated in FIG. 1. In this regard, the claims processor computer 108 may receive healthcare transactions and/or other communications from the service provider computer 106, and the claims processor computer 108 may communicate information associated with processing transactions to the service provider.

With continued reference to FIG. 1, any number of external data sources 110 may be provided. As desired, each data source 110 may include one or more computers that include components that are similar to those of other devices included in the system 100, such as the healthcare provider computer 104 or service provider computer 106. Each data source 110 may be configured or programmed to provide healthcare transaction information and/or information associated with the adjudication of healthcare transactions to the service provider computer 106 and/or the payor profile module 180. For example, a data source 110 may be a processor-driven device that is associated with another service provider, an entity that audits healthcare transactions, and/or a claims processor. As desired, data may be pulled from a data source 110 by the service provider computer 106 and/or the payor profile module 180. For example, a request for information may be provided to the data source 110, and information may be returned in response to the request. Additionally or alternatively, a data source 110 may push information to the service provider computer 106 and/or the payor profile module 180. For example, healthcare transaction information may be periodically communicated by the data source 110 at predetermined intervals, such as once a day, once a week, etc.

The healthcare provider back office computer 195 may be one or more computers associated with a group of healthcare providers, such as a chain of pharmacies. The healthcare provider back office computer 195 may include components that are similar to those of other devices included in the system 100, such as the healthcare provider computer 104. For example, the healthcare provider back office computer 195 may be a processor-driven device that is operable or configured to provide, to the service provider computer 106 and/or the payor profile module 180, any number of parameters, rules, and/or preferences associated with the generation of payor sheets based upon healthcare transaction information. Additionally, the healthcare provider back office computer 195 may be operable or configured to receive information associated with generated payor sheets and/or various reports and/or billing information associated with the generation of payor sheets.

The network 115 may include any telecommunication and/or data network, whether public, private, or a combination thereof, including a local area network, a wide area network, an intranet, the Internet, intermediate handheld data transfer devices, and/or any combination thereof and may be wired and/or wireless. The network 115 may also allow for real time, offline, and/or batch transactions to be transmitted between or among the healthcare provider computers 104a-n, the service provider computer 106, and the claims processor computers 108a-n. Due to network connectivity, various methodologies as described herein may be practiced in the context of distributed computing environments. Although the service provider computer 106 is shown for simplicity as being in communication with the healthcare provider computers 104a-n, and/or the claims processor computers 108a-n via one intervening network 115, it is to be understood that any other network configuration is possible. For example, intervening network 115 may include a plurality of networks, each with devices such as gateways and routers for providing connectivity between or among networks 115. Instead of or in addition to a network 115, dedicated communication links may be used to connect the various devices in accordance with an example embodiment of the invention. For example, the service provider computer 106 may form the basis of network 115 that interconnects the healthcare provider computers 104a-n and the claims processor computers 108a-n.

A payor profile module 180 or payor profile application may also be operative with the service provider computer 106. The payor profile module 180 may include computer-executable instructions for analyzing information associated with healthcare transactions, identifying data fields that are required or likely required by a payor or claims processor, and/or generating one or more payor sheets.

In operation, the payor profile module 180 may access and/or receive information associated with healthcare transactions that have been processed by one or more payors or claims processors. For example, healthcare transaction information and/or adjudicated reply information may be accessed from one or more databases 182 or data storage devices and/or from memory 142 associated with the service provider computer 106. As another example, information may be received from one or more external data sources 110. As desired, the access and/or receipt of information may be based at least in part upon one or more rules and/or parameters associated with the generation of a payor sheet, such as rules or preferences received from a healthcare provider. For example, a request to generate or update a payor sheet may be received from a healthcare provider, and the request may include one or more preferences for the generation of the payor sheet, such as a Banking Identification Number ("BIN") associated with a payor, a Processor Control Number ("PCN") associated with the payor, and/or a range of dates for evaluating healthcare transactions. As another example, one or more default rules may be utilized to generate payor sheets. For example, the payor profile module 180 may periodically generate payor sheets for different payors based upon default rules.

Once healthcare transaction information has been accessed and/or received, the payor profile module 180 may analyze at least a portion of the healthcare transaction information to generate a payor sheet for a payor. According to an aspect of the invention, the payor profile module 180 may analyze the healthcare transaction information in order to identify one or more data fields that a claims processor or payor requires or likely requires to be populated or filled in when a healthcare transaction is communicated to the payor for adjudication or processing. The required or likely required fields that are identified may be utilized by the payor profile module 180 to generate or update a payor sheet for the payor. A wide variety of suitable techniques may be utilized by the payor profile module 180 to identify required or likely required data fields. For example, required fields may be identified based upon usages of those fields in healthcare transactions that are submitted to the payor. In certain embodiments, healthcare transactions that have been approved by the payor may be identified. Once approved or paid healthcare transactions have been identified, a set of data fields that are included in the healthcare transactions may be identified. A respective usage for each of the identified data fields within the healthcare transactions may then be calculated or determined. For example, a number of transactions in which the field has been populated may be determined, and the determined number may be utilized in conjunction with a total number of the transactions to calculate a percentage usage of the data field. As one example, if a data field is populated in ninety (90) out of one hundred (100) analyzed transactions, then a usage of the data field will be calculated to be ninety percent (90%).

Once usages have been calculated for the data fields, the calculated usages may be utilized to determine which of the data fields are required or likely required by the payor. In certain embodiments, the calculated usage for each field may be compared to a threshold value in order to determine whether the field is a required field. A wide variety of threshold values may be utilized as desired in various embodiments of the invention, for example, a threshold value of eighty-five percent (85%), ninety percent (90%), or ninety-five percent (95%). As desired, a threshold value may be received from a healthcare provider. Alternatively, a default threshold value may be utilized. If the usage of a field meets or exceeds the threshold value, then the field may be identified as a required field and marked for inclusion in a payor sheet. Otherwise, the field may be identified as an unnecessary or unrequired field. One example of the calculation of usages for data fields is set forth in Table 1 below:

TABLE 1

Example Data Field Utilizations

| Field Identifier | Field Description | Utilization | Percentage Utilization |
|---|---|---|---|
| A1 | BIN Number | 5000 | 100.0% |
| A2 | Version/Release Number | 5000 | 100.0% |
| A3 | Transaction Code | 5000 | 100.0% |
| A4 | Processor Control Number | 5000 | 100.0% |
| A9 | Transaction Count | 5000 | 100.0% |
| B2 | Service Provider ID Qualifier | 5000 | 100.0% |
| B1 | Service Provider ID | 5000 | 100.0% |
| D1 | Date of Service | 5000 | 100.0% |
| AK | Software Vendor/Certification ID | 5000 | 100.0% |
| AM | Segment Identification | 5000 | 100.0% |
| C4 | Date of Birth | 5000 | 100.0% |
| C5 | Patient Gender Code | 28 | 0.6% |
| CA | Patient First Name | 185 | 3.7% |
| CB | Patient Last Name | 185 | 3.7% |
| CM | Patient Street Address | 120 | 2.4% |
| CN | Patient City Address | 120 | 2.4% |
| CO | Patient State/Province Address | 120 | 2.4% |
| CP | Patient Zip/Postal Code | 120 | 2.4% |
| C2 | Cardholder ID | 5000 | 100.0% |
| CC | Cardholder First Name | 4950 | 99.0% |
| CD | Cardholder Last Name | 4950 | 99.0% |
| C1 | Group ID | 5000 | 100.0% |
| C3 | Person Code | 4950 | 99.0% |
| C6 | Patient Relationship Code | 4950 | 99.0% |
| EM | Prescription/Service Reference Number Qualifier | 5000 | 100.0% |
| D2 | Prescription/Service Reference Number | 5000 | 100.0% |
| E1 | Product/Service ID Qualifier | 5000 | 100.0% |
| D7 | Product/Service ID | 5000 | 100.0% |
| E7 | Quantity Dispensed | 5000 | 100.0% |
| D5 | Days Supply | 5000 | 100.0% |
| D6 | Compound Code | 5000 | 100.0% |
| D8 | Dispense As Written (DAW)/ Product Selection Code | 5000 | 100.0% |
| DE | Date Prescription Written | 4980 | 99.6% |
| DJ | Prescription Origin Code | 25 | 0.5% |
| EZ | Prescriber ID Qualifier | 5000 | 100.0% |
| DB | Prescriber ID | 5000 | 100.0% |
| D9 | Ingredient Cost Submitted | 4785 | 95.7% |
| DC | Dispensing Fee Submitted | 4785 | 95.7% |
| DQ | Usual and Customary Charge | 4200 | 84.0% |
| DU | Gross Amount Due | 5000 | 100.0% |
| DN | Basis of Cost Determination | 16 | 0.3% |
| DX | Patient Paid Amount Submitted | 21 | 0.4% |

With reference to Table 1, utilization information is illustrated for the data fields included in five thousand (5,000) healthcare transactions that have been approved by a payor. For each data field, a field identifier, field description, utilization, and percentage utilization are illustrated. The utilization includes a number of times that the data field was populated within the 5,000 analyzed transactions. The percentage utilization is a calculation of a percentage usage of the data field within the analyzed transactions. Once these usages and/or percentage usages are calculated, the values may be compared to one or more threshold values in order to determine whether each field is a required field. Fields that are identified as required fields may then be marked for inclusion in a generated or updated payor sheet for the payor.

As another example of a technique that may be utilized to identify required data fields, healthcare transactions that have been rejected by a claims processor or payor may be identified. Once a healthcare transaction has been identified as rejected or declined, one or more reason codes associated with the rejection may be identified. In other words, a reason for the rejection may be identified. Based upon the one or more reason codes, a determination may be made as to whether the healthcare transaction was rejected by the payor due to a failure to include information in a specific data field or based upon the inclusion of improper or incorrect information in the data field. If it is determined that the transaction was rejected due to incorrect information in a data field or due to a failure to populate the data field, then the data field that triggered the rejection may be identified as a required data field. The data field may then be marked for inclusion in a generated or updated payor sheet for the payor.

Once the required or likely required data fields for a payor have been identified, a payor sheet for the payor may be generated or updated. The payor sheet may include information associated with the mixture of fields that are required by the payor to be populated when a healthcare transaction is submitted to the payor. Once a payor sheet has been generated or updated, the payor sheet may be communicated to one or more recipients by the service provider computer 106 or the payor profile module 180. A payor sheet may be communicated to any number of recipients, such as a healthcare provider computer 104 or a healthcare provider back office computer 195. In certain embodiments, a payor sheet may be communicated to a recipient based upon a request for the payor sheet that has been received from the recipient. In other embodiments, payor sheets may be periodically generated or updated and communicated to one or more recipients. In still other embodiments, payor sheets may be communicated to a healthcare provider when the healthcare provider implements a new transaction management system. As desired, the payor sheets may be utilized to generate one or more user interfaces and/or electronically fillable forms that may be implemented by a transaction management system. Additionally, a wide variety of different communication techniques may be utilized to communicate a payor sheet to the recipient, including but not limited to, email, short message service ("SMS") messaging, other electronic communications, snail mail, etc. A payor sheet may be pushed to a recipient by the payor profile module 180 or service provider computer 106, or, alternatively pulled from the payor profile module 180 by a recipient submitting a request for one or more reports. Additionally, in certain embodiments, a payor sheet may be made available for download from an appropriate web site or server, such as a web site hosted by the service provider computer 106.

The data storage devices 182 or databases may be operable to store data as well as information associated with various rules and/or parameters that may be utilized by the payor profile module 180. Examples of data that may be stored include, but are not limited to, healthcare transaction information, information associated with identified required fields, payor sheet information, etc. In certain embodiments, rules may be received from one or more other components of the system 100, such as the healthcare provider computer 104, and/or the healthcare provider back office computer 195, and at least a portion of the received rules may be stored. A wide variety of rules and/or parameters may be received and/or stored, including but not limited to, rules associated with the generation of payor sheets, rules associated with utilization thresholds, rules associated with dates and/or date ranges for analyzing healthcare transactions, and/or rules associated with sorting, filtering, and/or analyzing healthcare transaction information, etc. In addition to or as an alternative to utilizing certain rules associated with a healthcare provider or group of healthcare providers, one or more default rules may be accessed and utilized by the payor profile module 180. Additionally, in certain embodiments, the data storage devices 182 may be operable to store information associated with healthcare transactions, adjudicated replies, and/or processing performed by the service provider computer 106. In certain embodiments, the data storage devices 182 may additionally store billing information associated with the generation of payor sheets. Additionally, as desired, the data storage devices 182 may store various reports associated with the processing performed by the payor profile module 180. The data storage devices 182 may be accessible by the payor profile module 180 and/or the service provider computer 106.

In certain embodiments, the payor profile module 180 and/or the service provider computer 106 may be operable to generate one or more reports that are associated with processed healthcare transaction information and/or generated payor sheets. A wide variety of different types of reports may be generated as desired in various embodiments of the invention. Additionally, a wide variety of different information may be incorporated into generated reports, including but not limited to, required field information, information associated with changes in required fields, information associated with analyzed healthcare transactions, etc. Reports may be sorted or formatted utilizing a wide variety of different criteria, parameters, and/or techniques. Additionally, the payor profile module 180 and/or the service provider computer 106 may communicate or direct the communication of generated reports to one or more other components of the system 100, for example, the healthcare provider computer 104 and/or the healthcare provider back office computer 195. A wide variety of different techniques and/or software programs may be utilized to format a generated report. For example, a report may be formatted as a comma-separated-value ("csv") file, as a spreadsheet file, as a word processor file, as a text file, etc. Additionally, a wide variety of different communication techniques may be utilized to communicate a report to the recipient, including but not limited to, email, short message service ("SMS") messaging, other electronic communications, snail mail, etc. A report may be pushed to a recipient by the payor profile module 180 or other reporting module, or, alternatively pulled from the payor profile module 180 by a recipient submitting a request for one or more reports. Additionally, in certain embodiments, a report may be made available for download from an appropriate web site or server, such as a web site hosted by the service provider computer 106.

Messages, payor sheets, and/or reports that are generated by the payor profile module 180 and/or the service provider computer 106 may be communicated to a recipient (e.g., the healthcare provider computer 104, the healthcare provider back office computer 195, etc.) by the payor profile module 180 in either a direct or indirect manner. In certain embodiments, messages, payor sheets, and/or reports may be directly communicated to a recipient by the payor profile module 180 via one or more suitable networks 115. In other embodiments, the messages, payor sheets, and/or reports may be communicated by the payor profile module 180 to another component of the system 100, such as the service provider computer 106, for communication to a recipient. For messages, payor sheets, and/or reports that are communicated to a healthcare provider, the communications may be sent to the healthcare provider computer 104 and/or to another device associated with the healthcare provider, such as a facsimile/printing device.

The operations of the payor profile module 180 and/or the data storage devices 182 are described in greater detail below with reference to FIG. 4.

Those of ordinary skill in the art will appreciate that the system 100 shown in and described with respect to FIG. 1 is provided by way of example only. Numerous other operating environments, system architectures, and device configurations are possible. Other system embodiments can include fewer or greater numbers of components and may incorporate some or all of the functionality described with respect to the system components shown in FIG. 1. For example, in one embodiment, the service provider computer 106 (or other computer) may be implemented as a specialized processing machine that includes hardware and/or software for performing the methods described herein. In addition, at least a portion of the processor and/or processing capabilities of the service provider computer 106 and/or the payor profile module 180 may be implemented as part of a claims processor computer 108. Accordingly, embodiments of the invention should not be construed as being limited to any particular operating environment, system architecture, or device configuration.

Operational Overview

Figure 2:
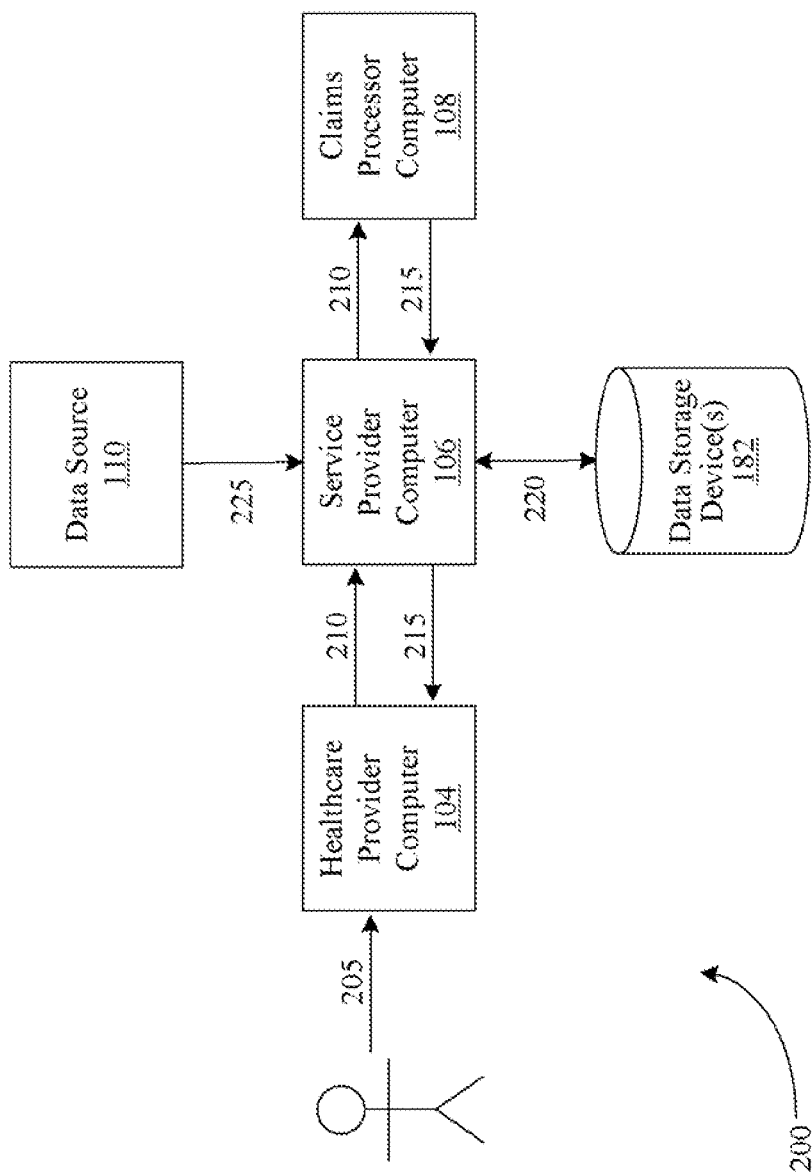
FIG. 2 is a block diagram of an example data flow for processing healthcare transactions as they are communicated through a service provider, according to an example embodiment of the invention.

FIG. 2 is a block diagram of an example data flow 200 for processing healthcare transactions as they are communicated through a service provider, such as the service provider computer 106 illustrated in FIG. 1. The data flow 200 may represent an example of routing a healthcare transaction received from a healthcare provider to a claims processor for adjudication. With reference to FIG. 2, a healthcare provider computer, such as a healthcare provider computer 104 illustrated in FIG. 1, may receive a healthcare request 205 from a patient. The healthcare request 205 may be a prescription order that is received in-person or electronically as desired in various embodiments of the invention. For example, a patient may seek to fill a prescription for one or more drugs, medications, and/or other products at a pharmacy location or store. As another example, a patient may communicate a healthcare request 205, such as a request to fill a prescription, to a healthcare provider computer 104 via one or more suitable network connections. For example, a purchase request may be communicated to a healthcare provider computer 104 from a customer computer via a web portal hosted by the healthcare provider computer 104. In addition, a physician/clinic/hospital computer can also communicate a healthcare request 205 as an electronic prescription order (e.g., an E-SCRIPT) to the healthcare provider computer 104.

The healthcare provider computer 104 may receive and process the request 205 to generate a healthcare transaction request 210, which may be in the form of a prescription claim request or an eligibility request. The generated healthcare transaction request 210 may be communicated by the healthcare provider computer 104 to the service provider computer 106. Accordingly, the healthcare transaction request 210 may be received by the service provider computer 106. According to an example embodiment of the invention, the healthcare transaction request 210 may be in accordance with a version of a National Council for Prescription Drug Programs ("NCPDP") Telecommunication Standard, although other standards may be utilized as well. As desired, the healthcare transaction request 210 may include a Banking Identification Number ("BIN") and/or Processor Control Number ("PCN") for identifying a claims processor computer, such as one of the claims processor computers 108*a-n* illustrated in FIG. 1, as a destination of the healthcare transaction request 210. In addition, the healthcare transaction request 210 may also include information relating to the patient, payor, prescriber, healthcare provider, and/or the prescribed drug or product. As an example, the healthcare transaction request 210 received by the service provider computer 106 may include one or more of the following information:

- Payor ID/Routing Information for each identified payor or potential payor
  - Banking Identification Number ("BIN") and Processor Control Number ("PCN") that designates an intended destination of the healthcare transaction request 210
- Patient Information
  - Name (e.g., Patient Last Name, Patient First Name, etc.)
  - Date of Birth of Patient
  - Age of Patient
  - Gender
  - Patient Address (e.g., Street Address, Zip Code, etc.)
  - Patient Contact Information (e.g., Patient Telephone Number)
  - Patient ID or other identifier
- Insurance/Coverage Information
  - Cardholder Name (e.g., Cardholder First Name, Cardholder Last Name)
  - Cardholder ID and/or other identifier (e.g., person code)
- Provider (e.g., Prescriber, Pharmacy) Information
  - Prescriber Information
  - Primary Care Provider ID or other identifier (e.g., National Provider Identifier ("NPI") code)
  - Primary Care Provider Name (e.g., Last Name, First Name)
  - Prescriber ID or other identifier (e.g., NPI code, DEA number)
  - Prescriber Name (e.g., Last Name, First Name)
  - Prescriber Contact Information (e.g., Telephone Number)
  - Pharmacy or other Healthcare Provider Information (e.g., store name, chain identifier, etc.)
  - Pharmacy or other Healthcare Provider ID (e.g., NPI code)
- Claim Information
  - Drug or product information (e.g., National Drug Code ("NDC"))
  - Prescription/Service Reference Number
  - Date Prescription Written
  - Quantity Dispensed
  - Number of Days Supply
  - Diagnosis/Condition
  - Pricing information for the drug or product (e.g., network price, Usual & Customary price)
  - Date of Service.

The service provider computer 106 may receive the healthcare transaction request 210 from the healthcare provider computer 104, and the service provider computer 106 may process the healthcare transaction request 210. As desired, the service provider computer 106 may perform one or more pre-edits on the healthcare transaction request 210. The pre-edits may verify, add, and/or edit information included in the healthcare transaction request 210 prior to the healthcare transaction request 210 being communicated to an appropriate claims processor computer, such as a claims processor computer 108 illustrated in FIG. 1. If no rejections are triggered or generated by any pre-edits performed for the transaction request 210, then the healthcare transaction request 210 and/or a copy thereof may be routed or otherwise communicated by the service provider computer 106 to an appropriate claims processor computer 108 associated with a designated payor for adjudication. According to an example embodiment, the service provider computer 106 may utilize at least a portion of the information included in the healthcare transaction request 210, such as a BIN/PCN, to determine the appropriate claims processor computer 108 to route the healthcare transaction request 210 to. The service provider computer 106 may also include a routing table, perhaps stored in memory, for determining which claims processor computer 108 to route the healthcare transaction request 210 to.

The claims processor computer 108 may receive and adjudicate or otherwise process the healthcare transaction request 210. For example, the claims processor computer 108 may determine benefits coverage for the healthcare transaction request 210 according to an adjudication process associated with eligibility, pricing, and/or utilization review. The claims processor computer 108 may transmit an adjudicated reply 215 or other response for the healthcare transaction request 210 to the service provider computer 106. The service provider computer 106 may receive the adjudicated reply 215 from the claims processor computer 108. As desired, the service provider computer 106 may perform any number of post-edits on the adjudicated reply 215. The service provider computer 106 may then route or otherwise communicate the adjudicated reply 215 or a copy thereof to the healthcare provider computer 104.

As desired, the service provider computer 106 may store information 220 associated with the healthcare transaction request 210 and/or the adjudicated reply 215 in one or more suitable data storage devices, such as the databases 182 illustrated in FIG. 1. Examples of information that may be stored include, but are not limited to, information included in the healthcare transaction request 210, information included in the reply 215, an indication of whether the transaction request 210 has been approved or paid, financial information associated with the transaction request 210 and/or processing of the transaction request 210, etc. The stored information 220 may be utilized for a wide variety of reporting and/or billing purposes.

Additionally, the service provider computer 106 may receive information 225 associated with the processing and/or adjudication of healthcare transactions from one or more external data sources, such as the data sources 110 illustrated in FIG. 1. For example, information associated with healthcare transactions that are not routed or communicated through the service provider computer 106 may be received from the data sources 110. In this regard, healthcare transaction information may be obtained for subsequent analysis by the payor profile module 180.

It will be appreciated that variations of the data flow 200 illustrated in FIG. 2 may be utilized in accordance with various embodiments of the invention. The data flow 200 of FIG. 2 is provided by way of example only.

Figure 3A:
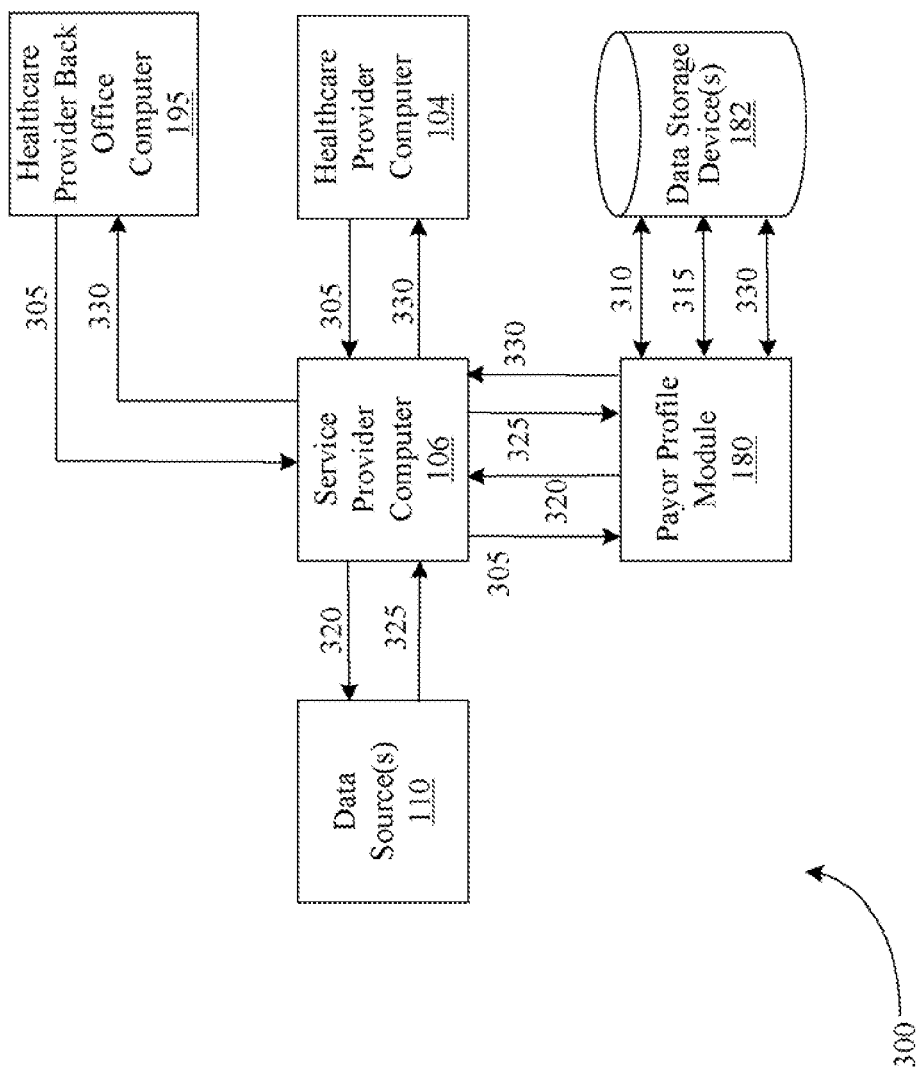
FIGS. 3A and 3B are block diagrams of example data flows for processing healthcare transaction information at a service provider in order to generate a payor sheet, according to example embodiments of the invention.

FIG. 3A is a block diagram of an example data flow 300 for processing healthcare transaction information at a service provider, such as the service provider computer 106 illustrated in FIG. 1, in order to generate or update one or more payor sheets, according to an example embodiment of the invention. With reference to FIG. 3A, a request 305 for a payor sheet may optionally be received by the service provider computer 106 and/or an associated payor profile module 180 from another entity, such as a healthcare provider. For example, a request 305 may be received from a healthcare provider computer, such as the healthcare provider computer 104 illustrated in FIG. 1, and/or from a healthcare provider back office computer, such as the healthcare provider back office computer 195 illustrated in FIG. 1. In certain embodiments, a received request 305 may include one or more rules and/or parameters 310 associated with the generation of a payor sheet, such as a BIN and PCN associated with a payor. As an alternative to receiving a request for one or more payor sheets, payor sheets may be periodically generated and/or updated by the service provider computer 106 and/or the payor profile module 180. Additionally, as desired, payor sheets may be dynamically updated and/or maintained by the service provider computer 106 and/or the payor profile module 180.

As desired, the payor profile module 180 may access one or more rules and/or parameters 310 from one or more data storage devices, such as the devices 182 illustrated in FIG. 1. The accessed rules and/or parameters 310 may be associated with the generation of a payor sheet. In certain embodiments, the accessed rules 310 may be stored rules that were previously received from a healthcare provider. For example, the rules 310 may have been previously received from the healthcare provider computer 104 and/or the healthcare provider back office computer 195. In other embodiments, at least a portion of the accessed rules 310 may be default rules. A wide variety of rules may be accessed as desired in various embodiments of the invention, such as rules identifying a payor (e.g., a BIN, a PCN, etc.), rules associated with a start date and/or date range of transactions to analyze, rules associated with a look-back period for analyzing transactions, rules associated with a number of transactions or number of previously processed transactions to analyze, rules associated with processing techniques that are utilized to identify required fields, utilization threshold parameters, rules associated with the formatting of a generated payor sheet, etc.

Once a payor for a payor sheet has been identified, the payor profile module 180 may obtain healthcare transaction information associated with the payor. As illustrated in FIG. 3A, stored healthcare transaction information 315, such as healthcare transaction records for the payor, may be accessed from the data storage devices 182. The accessed information 315 may include information associated with healthcare transactions and responses to healthcare transactions that have been routed or otherwise communicated through the service provider computer 106. Additionally, in certain embodiments, the accessed information 315 may include healthcare transaction records that have been received from one or more external data sources, such as the data sources 110 illustrated in FIG. 1.

As an alternative or in addition to accessing stored information 315 that has been received from one or more external data sources 110, the payor profile module 180 and/or the service provider computer 106 may request healthcare transaction information from the data source(s) 110, and healthcare transaction information may be received in response to one or more requests. For example a request 320 for healthcare transaction information may be generated by the payor profile module 180 and, the payor profile module 180 may direct the service provider computer 106 to communicate the request 320 to a data source 110. The request 320 may include information associated with one or more payors for which payor sheets will be generated, as well as any number of rules or parameters associated with the access, formatting, and/or provision of healthcare transaction information by the data source 110. For example, the request 320 may include parameters associated with the identified payor, date information for accessing healthcare transaction data, etc. In response to a request 320, the data source 110 may communicate healthcare transaction information 325 to the service provider computer 106 for provision to the payor profile module 180.

The payor profile module 180 may utilize at least a portion of the obtained healthcare transaction information 315, 325 in order to generate a payor sheet 330 for the payor. Based upon an analysis of the healthcare transaction information 315, 325, the payor profile module 180 may identify data fields that the payor requires or likely requires to be populated when submitting a healthcare transaction for processing by the payor. A wide variety of techniques may be utilized to analyze the healthcare transaction information 315, 325 in order to identify one or more required fields to include in a payor sheet 330. As one example, the healthcare transaction information 315, 325 may be sorted or filtered in order to identify transactions that have been approved or paid by the payor. The data fields that are included in these transactions may then be identified. Respective utilization information, such as a percentage usage, may be determined or calculated for each data field. Once usage information has been calculated for a data field, the usage information may be compared to one or more threshold parameters in order to determine whether the data field is a required or likely required field.

As another example of a technique for identifying required fields, healthcare transactions that have been rejected by the payor may be identified. Each rejected healthcare transaction may then be analyzed in order to determine or ascertain one or more reasons that triggered the rejection. For example, one or more respective reason codes associated with the rejections may be determined. Based upon the reasons or reason codes for a rejected transaction, a determination may be made as to whether the transaction was rejected for a failure to include information in a particular data field or for the inclusion of improper or incorrect information in the data field. If it is determined that the transaction was rejected for one of these two reasons, then the data field that led to the triggering of the rejection may be identified as a required data field. In other words, a determination may be made that the payor evaluates the data field when processing a healthcare transaction, and therefore, that the payor likely requires the data field to be populated.

Once the required fields for a payor have been identified, the payor profile module 180 may generate or update a payor sheet 330 for the payor based at least in part upon the identified required fields. The payor sheet 330 may include information associated with the mixture or combination of fields that are required by the payor to be populated when a healthcare transaction is submitted to the payor. Once a payor sheet 330 has been generated or updated, the payor profile module 180 may communicate or direct the communication of the payor sheet 300 to one or more recipients, such as the healthcare provider computer 104 or the healthcare provider back office computer 195. In certain embodiments, the payor sheet 330 may be communicated to a recipient in response to a received request 305 for the payor sheet 330. In other embodiments, the payor sheet 330 may be periodically generated or updated and communicated to one or more recipients. In still other embodiments, the payor sheet 330 may be communicated to a healthcare provider when the healthcare provider implements a new transaction management system. The payor sheet 330 may be communicated as a separate communication or, alternatively, in combination with one or more other payor sheets for different payors. As desired, the payor sheet 330 may be utilized to generate one or more user interfaces and/or electronically finable forms that may be implemented by a transaction management system. Additionally, a wide variety of different communication techniques may be utilized to communicate the payor sheet 330 to a recipient, including but not limited to, email, short message service ("SMS") messaging, other electronic communications, snail mail, etc. Additionally, in certain embodiments, the payor sheet 330 may be made available for download from an appropriate web site or server, such as a web site hosted by the service provider computer 106.

Additionally, as desired, the generated payor sheet 330 may be stored by the payor profile module 180 in the data storage devices 182. In this regard, the generated payor sheet 330 may be accessed at a subsequent point in time for updating and/or for communication to one or more recipients.

Figure 3B:
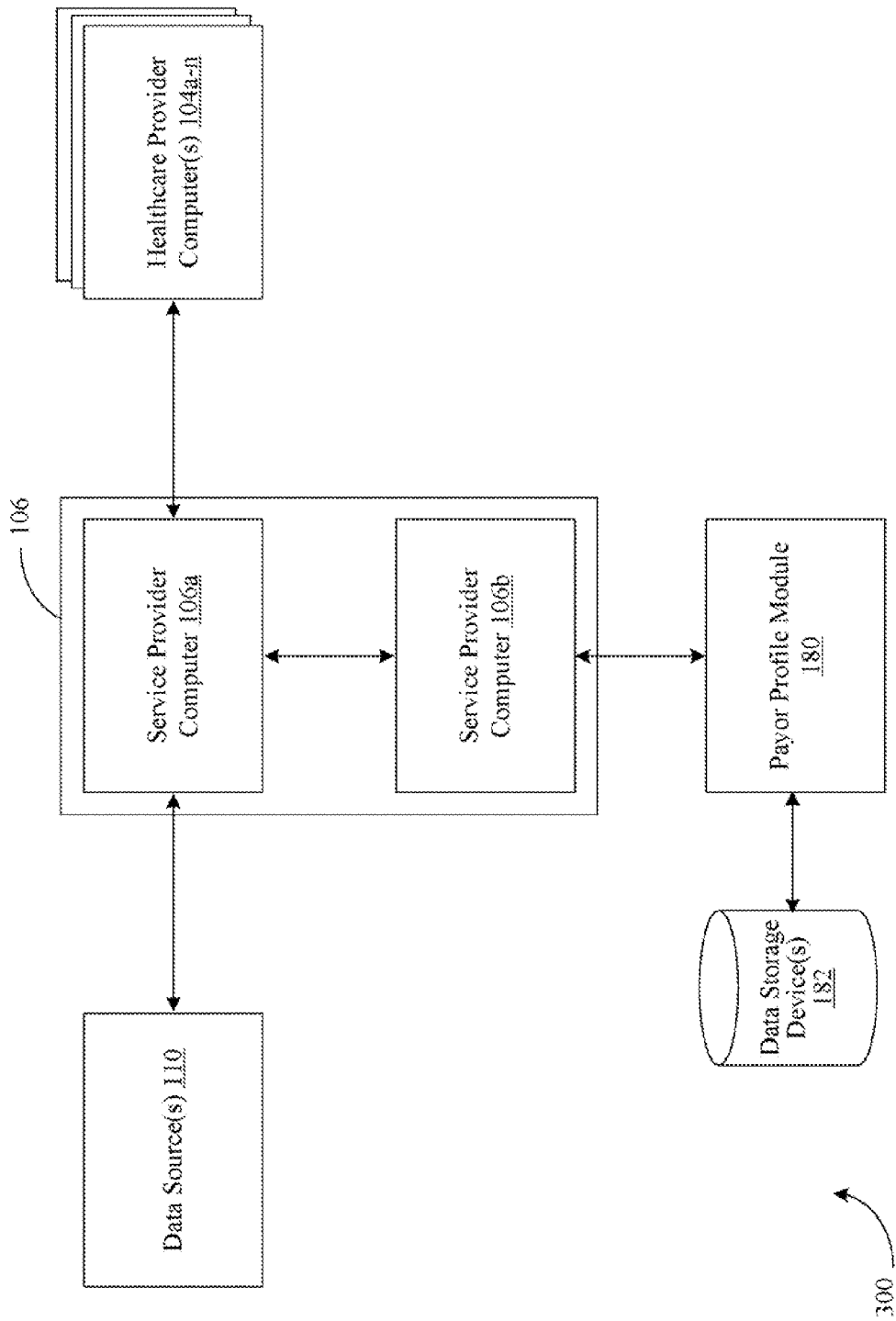

It will be appreciated that variations of the data flow 300 illustrated in FIG. 3A may be utilized in accordance with various embodiments of the invention. For example, as shown in FIG. 3B, the service provider computer 106 may be comprised of two or more distinct service provider computers 106*a* and 106*b* that are in communication with each other. Service provider computer 106*a* may be operative with one or more healthcare provider computers, data sources, and/or claims processor computers, such as the healthcare provider computers 104*a-n*, data sources 110, and/or claims processor computers 108*a-n* illustrated in FIG. 1. However, service provider computer 106*b* may have a data processing arrangement with service provider computer 106*a*. Under the data processing agreement, the service provider computer 106*a* may be permitted to utilize or offer services of the service provider computer 106*b*, including those of the payor profile module 180. For example, a first service provider may communicate healthcare transaction information and/or other information to a second service provider for processing and/or analysis in order to generate one or more payor sheets.

Figure 4:
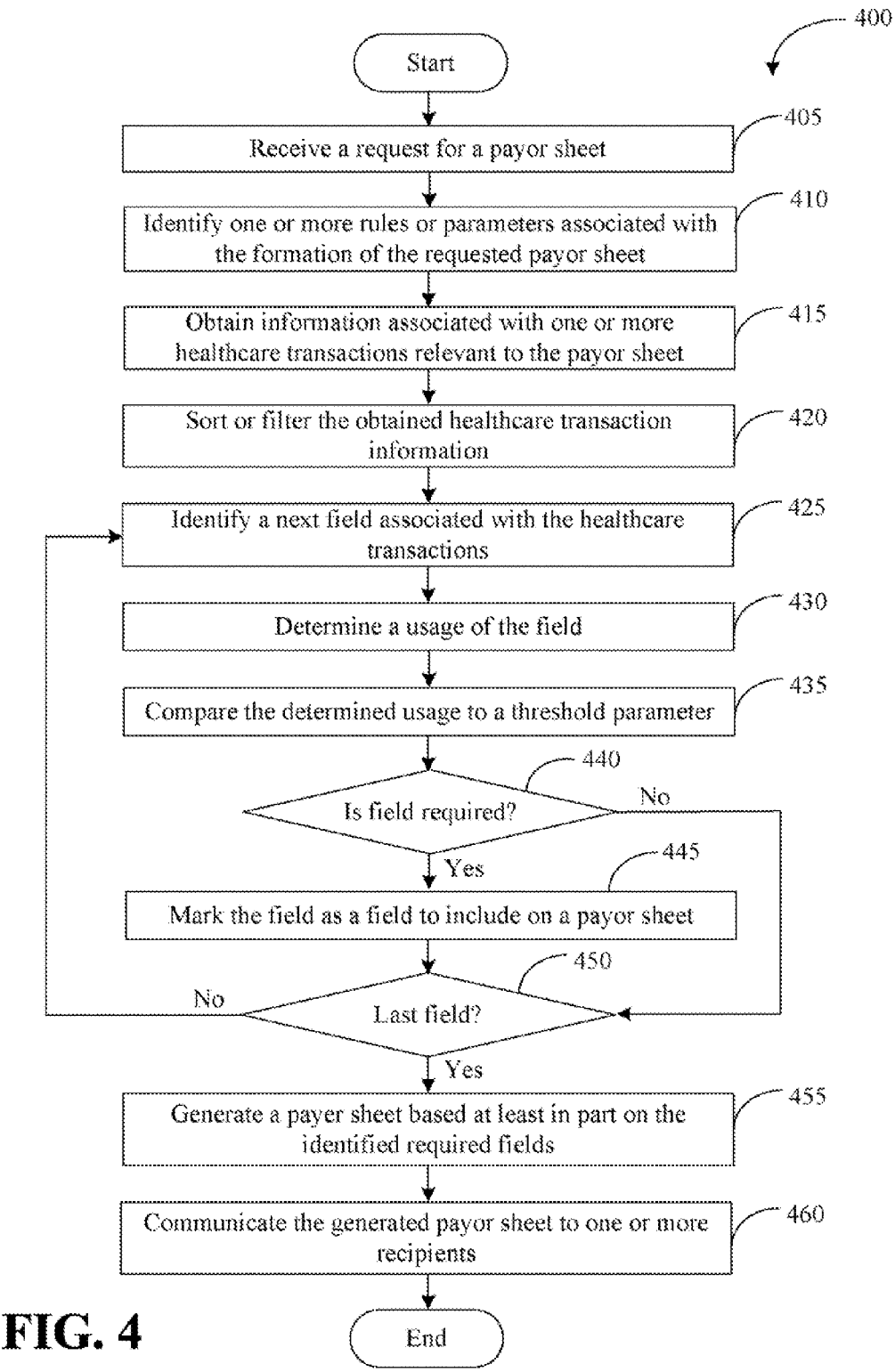
FIG. 4 is a flow diagram of an example method for generating a payor sheet, according to an example embodiment of the invention.

FIG. 4 is a flow diagram of an example method 400 for generating a payor sheet, according to an example embodiment of the invention. The method 400 may be performed by a suitable service provider computer and/or an associated payor profile module, such as the service provider computer 106 and the payor profile module 180 illustrated in FIG. 1. The method 400 may begin at block 405.

At block 405, which may be optional in certain embodiments of the invention, a request for one or more payor sheets may be received. For example, a request for one or more new and/or updated payor sheets may be received from a healthcare provider, such as a pharmacy or pharmacy chain. The request may identify one or more payors for which payor sheets are desired. A wide variety of information may be included in a request as desired in various embodiments of the invention, such as identifiers for one or more payors (e.g., BIN and/or PCN identifiers) and/or one or more rules or parameters associated with the generation of payor sheets.

At block 410, one or more rules or parameters associated with the formation or generation of a requested payor sheet may be identified. The rules or parameters may be received in the request and/or accessed from memory. Additionally, the rules may be rules that are received or that have been previously received from a healthcare provider. Alternatively, at least a portion of the rules may be default rules associated with the generation of one or more payor sheets. A wide variety of rules may be identified as desired in various embodiments of the invention. A wide variety of rules may be accessed as desired in various embodiments of the invention, such as rules identifying a payor (e.g., a BIN, a PCN, etc.), rules associated with a start date and/or date range of transactions to analyze, rules associated with a look back period for analyzing transactions, rules associated with a number of transactions or number of previously processed transactions to analyze, rules associated with processing techniques that are utilized to identify required fields, utilization threshold parameters, rules associated with the formatting of a generated payor sheet, etc.

At block 415, information associated with one or more healthcare transactions relevant to the generation of a payor sheet may be obtained. As desired, the healthcare transaction information may be obtained based upon an identity of a payor associated with the payor sheet (e.g., a BIN, PCN, and/or other identifier associated with the payor) and/or based upon the identified rules or parameters. For example, healthcare transaction information for a payor that is associated with a particular period of time or a particular historical period may be obtained. The obtained information may include information associated with healthcare transactions that have been submitted to the payor, information associated with the adjudication and/or processing of the transactions by the payor, and/or information associated with the disposition of the healthcare transactions. Additionally, the healthcare transaction information may be obtained from a wide variety of sources as desired in various embodiments of the invention. For example, healthcare transaction information may be accessed from one or more memory devices and/or data storage devices associated with the service provider computer 106 and/or the payor profile module 180. As another example, healthcare transaction information may be obtained from one or more external data sources, such as the external data sources 110 described above with reference to FIG. 1.

At block 420, which may be optional in certain embodiments of the invention, the obtained healthcare transaction information may be sorted or filtered in accordance with any number of criteria. For example, the healthcare transaction information may be filtered to remove information associated with healthcare transactions that have been rejected or not paid by the payor. In this regard, healthcare transactions that are evaluated based upon data field usage may be limited to approved healthcare transactions.

Each healthcare transaction may include a wide variety of data fields that were populated when the healthcare transaction was submitted to the payor. These data fields may be evaluated in order to determine which data fields the payor requires or likely requires to be populated when a healthcare transaction is submitted. A payor sheet may then be generated based at least in part upon the identified required fields. At block 425, a next data field that is included in or that has been populated in at least one of the healthcare transactions may be identified and selected. A usage for the selected data field may be calculated or determined at block 430. The calculated usage may represent a usage of the data field within the plurality or group of healthcare transactions that are being analyzed. For example, the calculated usage may represent a percentage usage of the data field within the healthcare transactions that have been approved by the payor. A wide variety of techniques may be utilized as desired to calculate a usage for the selected data field. For example, a number of times that the data field has been populated within the evaluated group of healthcare transactions may be determined. The determined number of times may then be utilized in conjunction with a total number of the evaluated transactions to calculate a percentage usage of the data field within the evaluated transactions. For example, if one thousand (1,000) healthcare transactions are evaluated and the selected data field is populated in nine hundred and fifty (950) of the transactions, then the usage of the selected data field may be calculated as ninety-five percent (95%).

At block 435, the calculated or determined usage for the selected data field may be compared to a predetermined usage threshold parameter. The threshold parameter may establish a minimum usage for a required data field. For example, if the threshold parameter is ninety percent (90%), then any data field having a calculated usage of ninety percent or greater may be identified as a required field. At block 440, a determination may be made as to whether the selected data field is a required or likely required data field of the payor. The determination may be made based upon the comparison of the calculated usage to the threshold parameter. If it is determined at block 440 that the selected data field is not a required field, then operations may continue at block 450 described in greater detail below. If, however, it is determined at block 440 that the selected field is a required data field, then operations may continue at block 445. At block 445, the selected field may be marked or identified as a required data field. In this regard, the selected field may be marked for inclusion in a payor sheet for the payor.

At block 450, a determination may be made as to whether the selected data field is the last data field associated with the evaluated healthcare transactions. If it is determined at block 450 that the selected data field is not the last data field, then operations may continue at block 425 and a next data field may be identified for analysis. If, however, it is determined at block 450 that the selected data field is the last data field, then operations may continue at block 455.

The identification of required fields based upon calculated usages of data fields is only one example of a suitable technique that may be utilized to identify required fields. A wide variety of other suitable techniques may additionally or alternatively be utilized as desired in various embodiments of the invention. For example, healthcare transactions that have been rejected or not paid by the payor may be identified. Each rejected healthcare transaction may be analyzed in order to determine or ascertain one or more reasons that triggered the rejection. For example, one or more respective reason codes associated with the rejections may be determined. Based upon the reasons or reason codes for a rejected transaction, a determination may be made as to whether the transaction was rejected for a failure to include information in a particular data field or for the inclusion of improper or incorrect information in the data field. If it is determined that the transaction was rejected for one of these two reasons, then the data field that led to the triggering of the rejection may be identified as a required data field. In other words, a determination may be made that the payor evaluates the data field when processing a healthcare transaction, and therefore, that the payor likely requires the data field to be populated.

At block 455, a payor sheet may be generated for the payor based at least in part on the identified required fields. The generated payor sheet may include information associated with a combination of fields that are required by the payor to be populated when a healthcare transaction is submitted to the payor. At block 460, which may be optional in certain embodiments of the invention, the generated payor sheet may be communicated to one or more recipients, such as to one or more healthcare providers. In certain embodiments, the payor sheet may be communicated to a recipient in response to a received request for the payor sheet. In other embodiments, the payor sheet may be periodically generated or updated and communicated to one or more recipients. In still other embodiments, the payor sheet may be communicated to a healthcare provider when the healthcare provider implements a new transaction management system. In other embodiments, the payor sheet may be made available for download from an appropriate web site or server, such as a web site hosted by the service provider computer 106. As desired, the payor sheet may be utilized to generate one or more user interfaces and/or electronically fillable forms that may be implemented by a transaction management system. These user interfaces and/or forms may be communicated to one or more recipients, such as to a healthcare provider that is implementing a new transaction management system.

The method 400 may end following block 460.

The operations described and shown in the method 400 of FIG. 4 may be carried out or performed in any suitable order as desired in various embodiments of the invention. Additionally, in certain embodiments, at least a portion of the operations may be carried out in parallel. Furthermore, in certain embodiments, less than or more than the operations described in FIG. 4 may be performed.

Example embodiments of the invention can provide the technical effects of creating a system, method, and apparatus that analyzes healthcare transaction information in order to generate, update, and/or maintain payor sheets for one or more payors. Additionally, example embodiments of the invention can provide the technical effect of providing payor sheets to one or more healthcare providers, such as one or more pharmacies. In this regard, healthcare provider mistakes in preparing healthcare transactions may be reduced and/or minimized, thereby leading to a relatively faster work flow on the part of the healthcare providers.

Various block and/or flow diagrams of systems, methods, apparatus, and/or computer program products according to example embodiments of the invention are described above. It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented, or may not necessarily need to be performed at all, according to some embodiments of the invention.

These computer-executable program instructions may be loaded onto a special purpose computer or other particular machine, a processor, or other programmable data processing apparatus to produce a particular machine, such that the instructions that execute on the computer, processor, or other programmable data processing apparatus create means for implementing one or more functions specified in the flow diagram block or blocks. These computer program instructions may also be stored in a computer-readable memory that can direct a computer or other programmable data processing apparatus to function in a particular manner, such that the instructions stored in the computer-readable memory produce an article of manufacture including instruction means that implement one or more functions specified in the flow diagram block or blocks. As an example, embodiments of the invention may provide for a computer program product, comprising a computer-usable medium having a computer-readable program code or program instructions embodied therein, said computer-readable program code adapted to be executed to implement one or more functions specified in the flow diagram block or blocks. The computer program instructions may also be loaded onto a computer or other programmable data processing apparatus to cause a series of operational elements or steps to be performed on the computer or other programmable apparatus to produce a computer-implemented process such that the instructions that execute on the computer or other programmable apparatus provide elements or steps for implementing the functions specified in the flow diagram block or blocks.

Accordingly, blocks of the block diagrams and flow diagrams support combinations of means for performing the specified functions, combinations of elements or steps for performing the specified functions, and program instruction means for performing the specified functions. It will also be understood that each block of the block diagrams and flow diagrams, and combinations of blocks in the block diagrams and flow diagrams, can be implemented by special-purpose, hardware-based computer systems that perform the specified functions, elements or steps, or combinations of special purpose hardware and computer instructions.

Many modifications and other embodiments of the invention set forth herein will be apparent having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A computer-implemented method, comprising:
   obtaining information associated with one or more healthcare transactions that have been processed by a payor;
   identifying a plurality of data fields included in the one or more healthcare transactions;
   calculating a respective usage of each of the identified data fields within the one or more healthcare transactions;
   identifying, based upon the calculated usages, one or more of the plurality of data fields as required fields, wherein a required field is a field required by the payor during the submission of a healthcare transaction; and
   generating, based at least in part upon the identified one or more required fields, a payor sheet associated with the payor,
   wherein the above operations are performed by one or more computers associated with a service provider.

2. The method of claim 1, wherein calculating a respective usage of each of the identified data fields comprises:
   determining a number of transactions included in the one or more healthcare transactions;
   determining a respective number of times that each of the identified data fields was populated within the one or more transactions; and
   calculating, based upon the number of transactions and the respective number of times, a respective percentage usage of each of the identified data fields.

3. The method of claim 1, wherein identifying one or more of the plurality of data fields as required fields comprises:
   comparing, for each of the identified data fields, the respective usage to a threshold parameter; and
   determining, based upon the comparison, whether the identified data field is a required field.

4. The method of claim 1, further comprising:
   identifying one or more rules associated with the generation of the payor sheet,
   wherein the information associated with one or more healthcare transactions is obtained based upon the identified one or more rules.

5. The method of claim 1, further comprising:
   filtering, prior to identifying the plurality of data fields, the one or more healthcare transactions to remove at least one rejected healthcare transaction.

6. The method of claim 1, wherein identifying one or more of the plurality of data fields as required fields further comprises:
   identifying at least one of the one or more healthcare transactions that has been rejected by the payor;
   determining that the at least one identified healthcare transaction was rejected based upon one of (i) a failure to include information in a data field or (ii) an inclusion of incorrect information in the data field; and
   identifying, based upon the determination, the data field as a required field.

7. The method of claim 1, wherein obtaining information associated with one or more healthcare transactions comprises at least one of (i) accessing stored information or (ii) obtaining information from at least one external data source.

8. The method of claim 1, further comprising:
   communicating the generated payor sheet to a healthcare provider.

9. A system, comprising:
   at least one memory operable to store computer-executable instructions; and
   at least one processor configured to access the at least one memory and execute the computer-executable instructions to:
      obtain information associated with one or more healthcare transactions that have been processed by a payor;
      identify a plurality of data fields included in the one or more healthcare transactions;
      calculate a respective usage of each of the identified data fields within the one or more healthcare transactions;
      identify, based upon the calculated usages, one or more of the plurality of data fields as required fields, wherein a required field is a field required by the payor during the submission of a healthcare transaction; and
      generate, based at least in part upon the identified one or more required fields, a payor sheet associated with the payor.

10. The system of claim 9, wherein the at least one processor is configured to calculate a respective usage of each of the identified data fields by executing the computer-executable instructions to:
    determine a number of transactions included in the one or more healthcare transactions;
    determine a respective number of times that each of the identified data fields was populated within the one or more transactions; and
    calculate, based upon the number of transactions and the respective number of times, a respective percentage usage of each of the identified data fields.

11. The system of claim 9, wherein the at least one processor is configured to identify one or more of the plurality of data fields as required fields by executing the computer-executable instructions to:
    compare, for each of the identified data fields, the respective usage to a threshold parameter; and
    determine, based upon the comparison, whether the identified data field is a required field.

12. The system of claim 9, wherein the at least one processor is further configured to execute the computer-executable instructions to:
    identify one or more rules associated with the generation of the payor sheet,
    wherein the information associated with one or more healthcare transactions is obtained based upon the identified one or more rules.

13. The system of claim 9, wherein the at least one processor is further configured to execute the computer-executable instructions to:
    filter, prior to the identification of the plurality of data fields, the one or more healthcare transactions to remove at least one rejected healthcare transaction.

14. The system of claim 9, wherein the at least one processor is further configured to identify one or more of the plurality of data fields as required fields by executing the computer-executable instructions to:
    identify at least one of the one or more healthcare transactions that has been rejected by the payor;

determine that the at least one identified healthcare transaction was rejected based upon one of (i) a failure to include information in a data field or (ii) an inclusion of incorrect information in the data field; and identify, based upon the determination, the data field as a required field.

15. The system of claim 9, wherein the information associated with one or more healthcare transactions is obtained from at least one of (i) one or more data storage devices associated with the at least one processor or (ii) at least one external data source.

16. The system of claim 9, wherein the at least one processor is further configured to execute the computer-executable instructions to:

direct the communication of the generated payor sheet to a healthcare provider.

17. A computer-implemented method, comprising:

storing information associated with a plurality of healthcare transactions that are communicated between one or more healthcare providers and one or more payors by a service provider;

accessing, based upon one or more parameters associated with the generation of a payor sheet, a subset of the plurality of healthcare transactions that are associated with a payor;

identifying a plurality of data fields included in the accessed subset of healthcare transactions;

calculating a respective usage of each of the identified data fields within the subset of healthcare transactions;

identifying, based upon the calculated usages, one or more of the plurality of data fields as required fields, wherein a required field is a field required by the payor during the submission of a healthcare transaction; and generating, based at least in part upon the identified one or more required fields, a payor sheet associated with the payor, wherein the above operations are performed by one or more computers associated with a service provider.

18. The method of claim 17, wherein calculating a respective usage of each of the identified data fields comprises:

determining a number of transactions included in the subset of healthcare transactions;

determining a respective number of times that each of the identified data fields was populated within the subset of healthcare transactions; and calculating, based upon the number of transactions and the respective number of times, a respective percentage usage of each of the identified data fields.

19. The method of claim 17, wherein accessing a subset of healthcare transactions based upon one or more parameters comprises accessing a subset of healthcare transactions based upon at least one of (i) a Banking Identification Number (BIN) or (ii) a Processor Control Number (PCN) associated with the payor.

20. The method of claim 17, further comprising:

communicating the generated payor sheet to a healthcare provider.

\* \* \* \* \*